(12) United States Patent
Bonne et al.

(10) Patent No.: US 8,003,056 B2
(45) Date of Patent: Aug. 23, 2011

(54) GAS ANALYZER APPARATUS AND METHOD OF ANALYZING GASES

(75) Inventors: Ulrich Bonne, Hopkins, MN (US); Patrick G. Hogan, Vernon Hills, IL (US); Richard A. Gorny, Des Plaines, IL (US); Leslie T. Ivie, Hawthorn Woods, IL (US)

(73) Assignee: Honeywell International Inc., Morristown, NJ (US)

( * ) Notice: Subject to any disclaimer, the term of this patent is extended or adjusted under 35 U.S.C. 154(b) by 801 days.

(21) Appl. No.: 11/762,891

(22) Filed: Jun. 14, 2007

(65) Prior Publication Data

US 2008/0311663 A1 Dec. 18, 2008

(51) Int. Cl.
*G01N 35/00* (2006.01)

(52) U.S. Cl. ............ 422/88; 422/83; 422/86; 422/90; 422/92; 422/98; 435/807; 436/167; 436/168; 73/23.2

(58) Field of Classification Search .......... 422/50–67, 422/83, 86, 88, 90–92, 98, 82.04; 435/807; 436/167, 168; 73/23.2
See application file for complete search history.

(56) References Cited

U.S. PATENT DOCUMENTS

| 2,602,729 | A | * | 7/1952 | Curry .................. 422/87 |
| 4,597,778 | A | | 7/1986 | Szonntagh |
| 4,617,277 | A | | 10/1986 | Bohl |
| 4,681,454 | A | | 7/1987 | Breemer |
| 4,806,491 | A | | 2/1989 | Heim |
| 4,913,881 | A | | 4/1990 | Evers |
| 4,935,206 | A | | 6/1990 | Helm |
| 5,091,642 | A | | 2/1992 | Chow |
| 5,232,664 | A | | 8/1993 | Krawzak et al. |
| 6,296,702 | B1 | * | 10/2001 | Bryning et al. ............ 118/401 |
| 2004/0175837 | A1 | * | 9/2004 | Bonne et al. .............. 436/164 |
| 2008/0138911 | A1 | * | 6/2008 | Robins ..................... 436/167 |

FOREIGN PATENT DOCUMENTS

| GB | 1 545 572 | 5/1979 |
| WO | WO 2006/061607 A1 | 6/2006 |

OTHER PUBLICATIONS

Extended European Search Report corresponding to Application No. EP 08 25 2025, dated Nov. 16, 2010.

* cited by examiner

*Primary Examiner* — Jill Warden
*Assistant Examiner* — Shogo Sasaki
(74) *Attorney, Agent, or Firm* — Husch Blackwell

(57) ABSTRACT

A gas analyzer apparatus includes a device or platform for supporting a predetermined quantity of a reagent capable of reacting with a predetermined gas to cause a detectable change in a characteristic of the reagent, a reservoir adapted to retain the reagent, a dispenser for dispensing a controlled quantity of the reagent from the reservoir to a predetermined position on the device for supporting the predetermined quantity of the reagent, and a detector that detects the presence of the predetermined gas upon the predetermined gas and the controlled quantity of reagent reacting to cause a detectable change in a characteristic of the reagent detectable by the detector, the detector adapted to detect a change in the controlled quantity of the reagent by detecting the change in the characteristic through the predetermined quantity of the reagent.

11 Claims, 2 Drawing Sheets

GAS ANALYZER APPARATUS AND METHOD OF ANALYZING GASES

FIELD OF THE INVENTION

The present invention generally relates to environment sensing, and more particularly, to apparatus and methods for detecting the presence of a gas.

BACKGROUND OF THE INVENTION

In recent times, greater emphasis has been placed on national home security and detecting threats to populations. In particular, detecting or sensing the presence of gases, particularly toxic gases, in the environment has become a priority, and a variety of detection systems and devices have been developed in response thereto. The detection of gases is also critical in certain industrial environments, particularly in clean room environments, such as in the production of semiconductors and microprocessors.

Industrial toxic gas monitors, as used e.g., in semiconductor processing, are required to be sensitive to gases at the parts per billion (ppb) level and specific to certain gases. Traditional analyzers are unwieldly with very long analyzing path lengths in order to reliably achieve ppb-level sensitivities. Therefore, a family of analyzers based on color-changing reactions on paper have been developed and accepted in the market. However, these analyzers require reagent bearing paper, which requires replacement of the paper bearing or on which reagent is placed for each subsequent test. Additionally, paper, even non-woven paper, is not an ideal surface on which to place reagents as the surface has a microscopically non-uniform texture.

Accordingly, it is desirable to provide an analyzer for detecting the presence of a gas, particularly a toxic gas, in an environment, which does not require the use of paper or other consumable material as the reagent supporting surface. In addition, it is desirable to provide an analyzer in which at least a portion of the detection apparatus can be positioned beneath and isolated from the reagent supporting surface, so that detection, particularly optical detection, can be performed through the reagent. Other desirable features and characteristics of the present invention will become apparent from the subsequent detailed description of the invention and the appended claims, taken in conjunction with the accompanying drawings and this background of the invention.

SUMMARY

In accordance with the present invention, a gas analyzer apparatus includes a device for supporting a predetermined quantity of a reagent capable of reacting with a predetermined gas to cause a detectable change in a characteristic of the reagent, a reservoir adapted to retain the reagent, a dispenser for dispensing a controlled quantity of the reagent from the reservoir to a predetermined position on the device for supporting the predetermined quantity of the reagent, and a detector that detects the presence of the predetermined gas upon the predetermined gas and the controlled quantity of reagent reacting to cause a detectable change in a characteristic of the reagent detectable by the detector, the detector adapted to detect a change in the controlled quantity of the reagent by detecting the change in the characteristic through the predetermined quantity of the reagent.

It is preferable in accordance with the present invention that the device for supporting the controlled quantity of reagent is reusable, eliminating the inconvenience and cost of frequently replacing the device, and that the controlled quantity of reagent is supported in a position that permits elements of the detector to be positioned above and below the reagent in order that a change in a characteristic of the reagent upon reacting with the predetermined gas, e.g. a change in color, can be easily and accurately detected. The "supporting device" as used herein is understood to refer to a structure of relatively uniform thickness having at least one substantially planar surface on or into which reagent can be deposited.

In one embodiment of this invention, the supporting device is in the form of a rotatable disk, which may be similar in shape to a compact disk, popularly known as a CD in the music recording industry. The preferred material of the disk is glass or a transparent, relatively impervious polymer, such as polyvinyl chloride, polyethylene or polytetrafluoroethylene, the latter popularly known and marketed as Teflon®.

In another embodiment of this invention, the supporting device is in the form of an elongated or disk-like structure having at least one orifice into which the controlled quantity of reagent is dispensed by the dispenser and held in the orifice by capillary forces. The orifice in this embodiment is sized to enable capillary forces to retain the quantity of reagent without the reagent falling through the orifice until a force is applied to cause the reagent to pass out of the orifice. It is more preferable for the supporting device in this embodiment to have a plurality of orifices spaced from each other into which controlled quantities of reagent can be dispensed and held therein by capillary forces.

In still another embodiment, the disk or elongated structure can be of a material which is non-reactive to the reagent, such as a gold alloy or platinum. The structure can be solid, in which case detection can be accomplished by observing the reflectance of the change of the characteristic of the reagent upon reaction with the predetermined gas, or the structure can contain orifices sized to retain controlled quantities of reagent by capillary forces, and the change in a characteristic of the reagent upon reaction with the gas observed or measured through the quantity of reagent.

Existing reagents which are known to react with specific gases can be used in the apparatus and method of the present invention. For example, reagents utilized in CHEMCASSETTE® paper or cartridges, (trademark of Zellweger Luwa AG Corporation) can be used as reagents in accordance with the present invention. CHEMCASSETTE® products are marketed by Honeywell Analytics, Inc., 405 Barclay Boulevard, Lincolnshire, Ill. 60069, USA.

The reagent reservoir is preferably a cartridge of the type generally used for printer ink or toner with a seal placed after the reservoir has been filled. As will be shown in the accompanying drawings, the dispenser includes apparatus for supporting the reservoir and for puncturing the seal and conducting reagent to the portion of the dispenser which dispenses a controlled quantity of reagent.

The dispenser in accordance with this invention preferably is a wire-piston device which is fluidly connected by a conduit to the reservoir, such that when the wire-piston is raised a controlled amount of reagent can enter the area of the conduit beneath the raised wire-piston, and when the wire-piston is lowered, the controlled quantity of reagent is ejected by the wire-piston from the conduit through an opening therein onto the predetermined position of the supporting device. The dispenser is preferably provided with seals to contain the reagent. In one embodiment, the dispenser is an ink jet print head and is adapted to eject one drop of reagent onto the predetermined position of the supporting device.

In a preferred embodiment of this invention, the gas analyzer includes apparatus to remove reagent from the reusable supporting device following the detector, and the method of the invention includes the step of removing reagent from the supporting device following the detecting step. The apparatus may include apparatus to remove droplets of reagent from the platform. The apparatus may include apparatus to remove droplets of reagent from the one surface of the platform. The removing apparatus may be a cloth and the method of removing comprising wiping the surface with a cloth where the reagent has been dispensed onto the surface of the supporting device, and/or rinsing the surface with water, if the reagent is water soluble, or with a solvent if it is not. Where the reagent has been dispensed into orifices in the supporting device, the removal apparatus can be a second wire-piston device capable of ejecting the reagent from each orifice following the detecting operation. The apparatus may include apparatus to remove droplets of reagent from the pluralities of orifices in the platform. The supporting device can be periodically rinsed as noted above, if desired.

Where the reaction of the reagent with the gas to be detected provides an observable color change, the detector includes a coherent light source and a photo-detector or microspectrometer that can detect, and preferably record the change in the wavelength of the light beam passing through or reflected by the controlled quantity of reagent.

BRIEF DESCRIPTION OF THE DRAWINGS

The present invention will hereinafter be described in conjunction with the following drawings figures, wherein like numerals denote like elements.

DETAILED DESCRIPTION OF PREFERRED EMBODIMENTS

The following detailed description of the invention is merely exemplary in nature and is not intended to limit the invention or the application and uses of the invention. Furthermore, there is no intention to be bound by any theory presented in the preceding background or the summary of the invention or the following detailed description of the invention.

Figure 1:
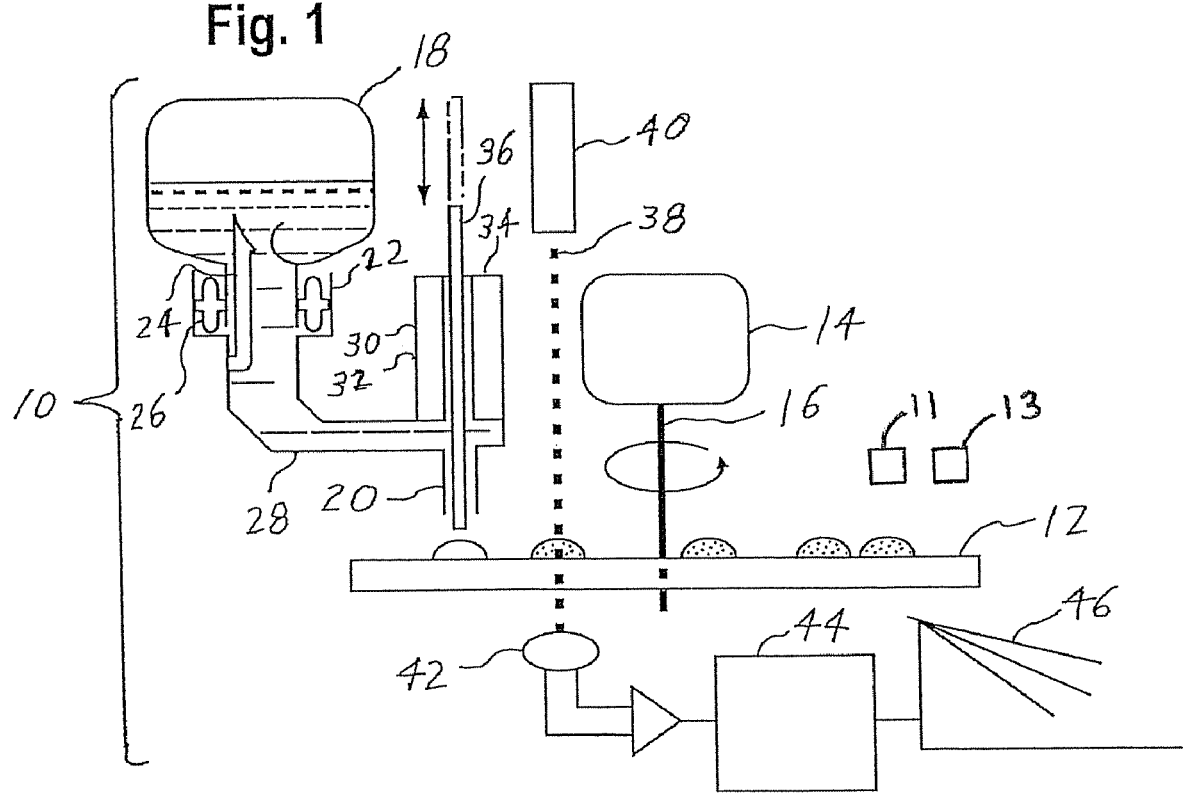
FIG. 1 is a schematic diagram of a gas analyzer apparatus in accordance with an illustrated embodiment of the invention.

Referring now to the drawings, FIG. 1 is a schematic diagram of a gas analyzer apparatus 10 in accordance with an exemplary embodiment of the present invention. The apparatus 10 comprises a device or platform 12 for supporting a predetermined quantity of a reagent capable of reacting with a predetermined gas to cause a change in a characteristic of the reagent, in this embodiment a color change of the reagent. As shown in FIG. 1, in this embodiment the platform 12 is a transparent circular disk of glass which is rotatable stepwise by a motor 14 coupled to platform 12 by a shaft 16.

A reservoir, in this embodiment a cartridge 18, similar to an ink cartridge for an ink-jet printer, holds a quantity of reagent, and is sealed until installed in the apparatus 10. A dispenser 20 includes a reservoir receiving support portion 22 having a seal piercing member 24 and a seal, such as an O-ring 26, to seal the reservoir 18 to the support portion 22 against ambient air entering the reservoir and the dispenser 20. Dispenser 20 includes a conduit 28 integral with receiving portion 22 and leading to a drop dispenser 30 also integral with conduit 28. Drop dispenser 30, in this embodiment comprises a wire dispenser 32. Wire dispenser 32 has a solenoid 34 which upon activation causes the wire or ram 36 of the dispenser to raise to allow a predetermined quantity of reagent in conduit 28 to enter the space in conduit 28 normally closed and sealed by the wire 36 passing through conduit 28. Upon the wire 36 dropping downward, the quantity of reagent in conduit 28 under the lower end of wire 36 is dispensed onto the platform 12. The wire 36 and the openings in the conduit 28 through which wire 36 passes are sized to admit and dispense a droplet of reagent onto the platform, whereas the wire 36 substantially seals the openings in the conduit when in the downward position. The position of the dispensed droplet of reagent on the platform is determined by rotation of the platform by the motor 14.

Upon rotation of the platform 12, the dispensed droplet of reagent is positioned in the path of a beam 38 from a coherent light source 40. Beam 38 passes through the droplet of reagent and through the transparent platform 12 to a photodetector or a microspectrometer 42 (e.g. a photodiode) which is electronically coupled to an electronics module 44. The electronic module 44 is adapted to generate a color change plot, denoted by reference numeral 46 in FIG. 1. In the presence of a predetermined gas which causes a reaction with the droplet of reagent, a change in the color of the reagent will occur and will be detected by the photodetector or microspectrometer and will be observable on the color change plot.

In a preferred embodiment of this invention, the gas analyzer includes apparatus to remove droplets of reagent from the reusable supporting device following the detector, and the method of the invention includes the step of removing reagent from at least one surface of the supporting device following the detecting step. The removing apparatus may be a cloth and the method of removing comprising wiping the surface with a cloth 11 where the reagent has been dispensed onto the surface of the supporting device, and/or rinsing the surface with water 13, if the reagent is water soluble, or with a solvent 13 if it is not.

Figure 2:
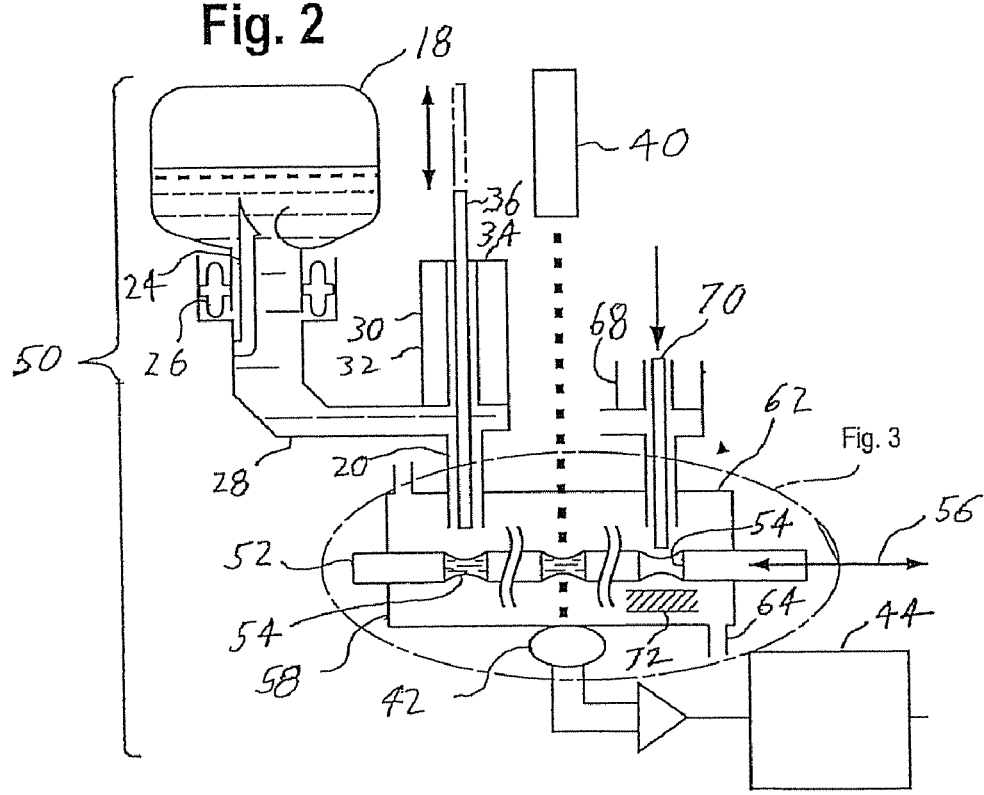
FIG. 2 is a schematic diagram of a gas analyzer apparatus in accordance with another exemplary embodiment of the present invention.
Figure 3:
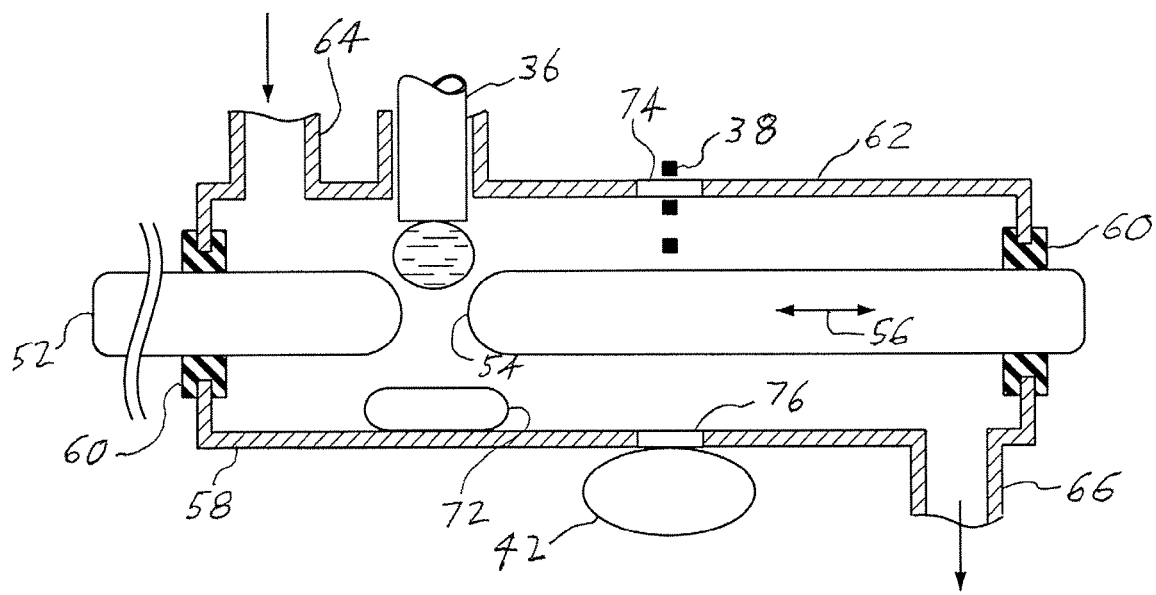
FIG. 3 is a schematic diagram of a portion of the gas analyzer apparatus shown in FIG. 2 by the broken line oval designated FIG. 3 in FIG.
Figure 4:
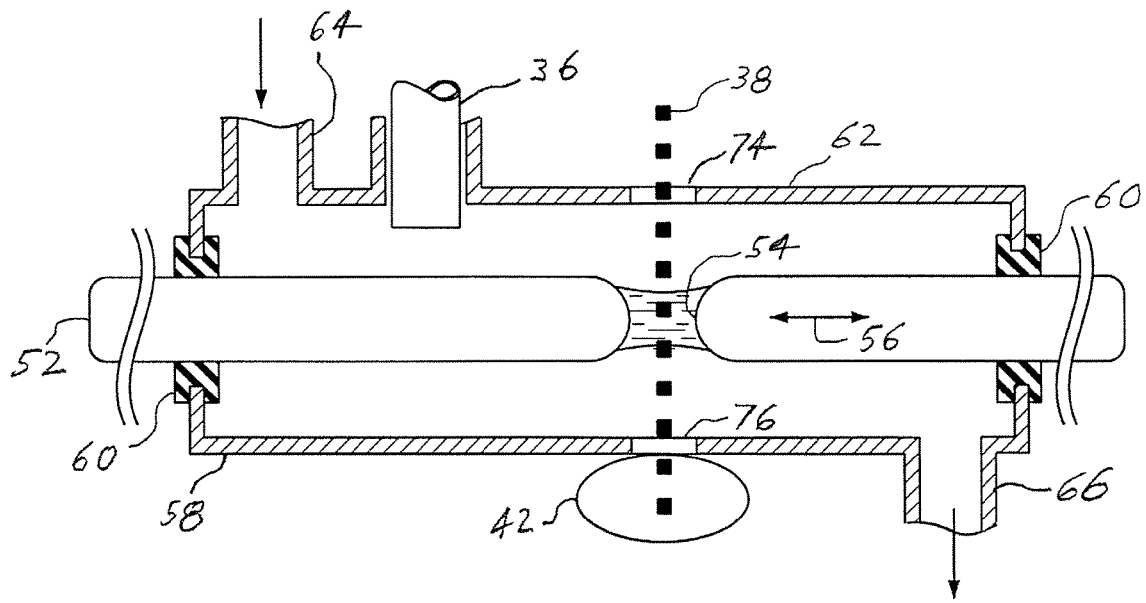
FIG. 4 is a schematic diagram as in FIG. 3 of the designated portion with the apparatus in another position.

FIGS. 2-4 illustrate schematically another embodiment of the present invention, wherein elements which are identical to elements in the first embodiment shown in FIG. 1, have the same reference numerals and are not explained further for the sake of brevity. In this embodiment generally noted by the numeral 50, the platform 52 is an elongated strip, instead of a disk as is platform 12 in the embodiment shown in FIG. 1. Platform 52 has a series of orifices 54 into which droplets of reagent are dispensed by the same apparatus as in the embodiment shown in FIG. 1, and are held therein by capillary forces as explained above. In this embodiment, platform 52 can be opaque or transparent, and if opaque can be of material, such as metals like gold alloy or platinum which do not react with the reagent. If platform 52 is transparent, it can be fashioned of the same materials as described herein for the first embodiment. Whereas in the first embodiment herein platform 12 was rotated by motor 14, in this embodiment platform 52 is moved reciprocally as indicated by arrow 56, by hand or by a motor and gears (not shown) in stepwise reciprocal fashion as is well known in the art. The platform 52 and the lower portion of dispenser 20 are enclosed by walls or a septum 58 with seals 60 (FIGS. 3 and 4) to provide an enclosed, low-dead-volume sample stage 62 having a gas sample inlet 64 and a gas sample outlet 66. As in the previously explained embodiment, after a droplet of reagent has been dispensed into or onto the platform, the droplet on the platform or in the orifice is moved to the detecting position where the beam 38 passes through the droplet and a color change of the droplet will occur if a reaction with a predetermined gas and will be detected by the photodetector or microspectrometer 42 and the electronics module 44 coupled to the photodetector or microspectrometer 42. A color change plot (not shown) will be generated if a color change has occurred.

FIG. 2 further illustrates an embodiment of this invention wherein reagent is removed from the orifices 54 in platform 50. The apparatus which performs the removal includes a second wire-piston 68, which can be identical to wire piston 32, by wire 70 passing through the orifice forcing the reagent out of the orifice and onto a disposable pad 72, which is subsequently removed from the analyzer as waste material and replaced.

FIGS. 3 and 4 show an embodiment wherein both the dispensing of the droplet of reagent into an orifice 54 and the removal of a droplet from an orifice 54 is provided by the same drop dispenser 30, acting sequentially upon different orifices. In FIG. 3 the droplet of reagent is being dispensed into the orifice 54. In FIG. 4 the droplet in the orifice 54 is being detected for reaction with a sample of gas having entered into the septum 58 through inlet 64 by a beam of light 38 passing therethrough via openings or windows 74 and 76.

In still another embodiment, if the platform 12 or 52 is opaque, but reflective, and without orifices, a color change in the droplets of reagent can be detected by having the photodetector or microspectrometer 42 positioned on the same side of the platform as the droplets, (not shown), but an angle to the beam 38 and having the photodetector or microspectrometer read the color change in the droplet upon the reflection of the color of the droplets from the platform surface.

Specific embodiments of a gas analyzer have been described for the purpose of illustrating the manner in which possible alternatives of the invention are made and used. It should be understood that the implementation of other variations and modifications of embodiments of the invention and its various aspects will be apparent to one skilled in the art, and that the various alternative embodiments of the invention are not limited by the specific embodiments described. Therefore, it is contemplated to cover all possible alternative embodiments of the invention and any and all modifications, variations, or equivalents that fall within the true spirit and scope of the basic underlying principles disclosed and claimed herein.

The invention claimed is:

1. A gas analyzer apparatus comprising:
   (a) a reusable, substantially non-pervious platform including a plurality of orifices;
   (b) a reservoir of a reagent capable of reacting with a predetermined gas to cause a detectable change in a characteristic of the reagent;
   (c) a dispenser that dispenses a controlled quantity of the reagent as a droplet from the reservoir into one of the plurality of orifices on the platform, wherein the droplet is retained in the orifice by capillary action;
   (d) an optical source adjacent the non-pervious platform that emits a beam of light; and
   (e) a chemical signature detector that detects the presence of the predetermined gas within the droplet on the platform in response to the predetermined gas and the controlled quantity of the reagent reacting to cause a detectable change in a characteristic of the reagent and a change in a wavelength of the beam of light passing through the droplet and detected by the detector.

2. The gas analyzer as in claim 1, wherein the reusable platform is transparent.

3. The gas analyzer as in claim 1, wherein the platform comprises a rotatable disk of transparent material.

4. The gas analyzer as in claim 2, wherein the transparent, reusable platform is selected from the group consisting of glass and a transparent, substantially impervious polymer.

5. The gas analyzer as in claim 4, wherein the polymer is selected from the group consisting of polyvinyl chloride, polyethylene and polytetrafluoroethylene.

6. The gas analyzer as in claim 1, wherein the dispenser is a wire-piston dispenser capable of dispensing a drop-size controlled quantity of the reagent from the reservoir to a predetermined position on one surface of the platform.

7. The gas analyzer as in claim 1, wherein the platform is a transparent disk, and the dispenser is capable of dispensing a drop-size controlled quantity of the reagent from the reservoir to one surface of the platform.

8. The gas analyzer as in claim 1, wherein the dispenser is capable of dispensing a drop-size controlled quantity of the reagent from the reservoir into the orifice of the platform.

9. The gas analyzer as in claim 1, further comprising apparatus to remove said droplets of said reagent from the platform.

10. The gas analyzer as in claim 3, further comprising apparatus to remove the droplets of the reagent from the one surface of the platform.

11. The gas analyzer as in claim 1, further comprising apparatus to remove the droplets of the reagent from the pluralities of said orifices in the platform.

* * * * *